(12) United States Patent
Schönfuss et al.

(10) Patent No.: US 10,247,692 B2
(45) Date of Patent: Apr. 2, 2019

(54) REFERENCE ELECTRODE ASSEMBLY FOR ELECTROCHEMICAL SENSOR AND ELECTROCHEMICAL SENSOR

(71) Applicant: HAMILTON BONADUZ AG, Bonaduz (CH)

(72) Inventors: Dirk Schönfuss, Tamins (CH); Philipp Arquint, Bonaduz (CH); Clara Caminada-Cavelier, Chur (CH)

(73) Assignee: HAMILTON BONADUZ AG, Bonaduz (CH)

( * ) Notice: Subject to any disclaimer, the term of this patent is extended or adjusted under 35 U.S.C. 154(b) by 110 days.

(21) Appl. No.: 15/326,460

(22) PCT Filed: Jul. 15, 2015

(86) PCT No.: PCT/EP2015/066130
§ 371 (c)(1),
(2) Date: Jan. 13, 2017

(87) PCT Pub. No.: WO2016/008908
PCT Pub. Date: Jan. 21, 2016

(65) Prior Publication Data
US 2017/0199145 A1    Jul. 13, 2017

(30) Foreign Application Priority Data
Jul. 16, 2014    (DE) .......................... 10 2014 109 995

(51) Int. Cl.
*G01N 27/403* (2006.01)
*G01N 27/30* (2006.01)
(Continued)

(52) U.S. Cl.
CPC ........... *G01N 27/301* (2013.01); *G01N 27/36* (2013.01); *G01N 27/4035* (2013.01);
(Continued)

(58) Field of Classification Search
CPC ......................... G01N 27/4035; G01N 27/301
See application file for complete search history.

(56) References Cited

U.S. PATENT DOCUMENTS

| 3,103,480 A |   | 9/1963 | Watanabe et al. |
|---|---|---|---|
| 4,120,292 A | * | 10/1978 | LeBlanc, Jr. ...... A61B 5/14539 |
|   |   |   | 204/403.06 |

(Continued)

FOREIGN PATENT DOCUMENTS

| CN | 102565165 A | 7/2012 |
|---|---|---|
| CN | 102590532 A | 7/2012 |

(Continued)

OTHER PUBLICATIONS

Galster, "pH-Messung (translated as pH-Measurement)," Wiley-VCH, Weinheim, Germany, 1990, pp. 82-97, 10 pages.

*Primary Examiner* — Alexander S Noguerola
(74) *Attorney, Agent, or Firm* — Seed Intellectual Property Law Group LLP (57) ABSTRACT

A reference electrode assembly for an electrochemical sensor, in particular for a potentiometric sensor, comprising a reference half-cell space having a reference electrode provided therein, the reference half-space comprising a storage space in which a reference electrolyte is provided at any rate in a storage state of the reference electrode assembly, the reference half-cell space further comprising a lock space that is permeable at any rate with respect to the passage of reference electrolyte into an environment of the reference half-cell space, the storage space, in the storage state of the reference electrode assembly, being separated from the lock space with respect to the passage of reference electrolyte, the reference electrode assembly being designed such that a connection permeable for the passage of reference electrolyte from the storage space to the lock space can be created (Continued)

between the storage space and the lock space in order to transfer the reference electrode assembly from the storage state to an operative state.

18 Claims, 3 Drawing Sheets

(51) Int. Cl.
 *G01N 27/36* (2006.01)
 *G01N 27/416* (2006.01)
(52) U.S. Cl.
 CPC ..... *G01N 27/4161* (2013.01); *G01N 27/4167* (2013.01); *G01N 27/4168* (2013.01)

(56) References Cited

U.S. PATENT DOCUMENTS

| | | | | |
|---|---|---|---|---|
| 4,272,245 A | * | 6/1981 | Diamond | G01N 27/4165 204/433 |
| 4,981,567 A | | 1/1991 | Wolcott | |
| 2011/0147213 A1 | * | 6/2011 | Auerswald | G01N 27/36 204/415 |

FOREIGN PATENT DOCUMENTS

| | | |
|---|---|---|
| CN | 103376285 A | 10/2013 |
| DE | 102010063031 A1 | 6/2012 |
| DE | 102013101735 A1 | 10/2013 |

* cited by examiner

REFERENCE ELECTRODE ASSEMBLY FOR ELECTROCHEMICAL SENSOR AND ELECTROCHEMICAL SENSOR

BACKGROUND

Technical Field

The present invention relates to the field of electrochemical sensors. Such sensors are utilized for analysis of, in particular, liquid process media in order to quantitatively determine specific properties of the process medium, in particular the pH value, the redox potential and/or the presence of certain ion species in the process medium. The properties that can be determined by means of electrochemical sensors will be summarized in the following under the term "electrochemical measurement variable".

Description of the Related Art

For determining electrochemical measurement variables there are used suitable measuring electrodes having the property that, upon contact of the measuring electrode with the process medium, an electrochemical potential is created that is dependent upon the respective electrochemical variable to be determined, e.g., the pH value or the concentration of a specific ion species. This potential is sensed in the form of a measurement signal, so that such sensors are also referred to as potentiometric sensors. The measuring electrode may be in the form of an ion-selective electrode that establishes direct contact with the process medium to be investigated, so that the ion-selective electrode and the process medium directly constitute a redox system the electrochemical potential of which is dependent on the concentration of a specific ion species in the process medium. However, in many cases the measuring electrode itself will already comprise a system of a sensing electrode in contact with an inner electrolyte, with the inner electrolyte then establishing electrolytic contact with the process medium. For example, in case of pH electrodes, a potential difference dependent on the pH value of the process medium as a rule is measured via a glass membrane situated between the process medium and the inner electrolyte of the measuring electrode. The inner electrolyte then constitutes a buffer system and is selected such that an electrical potential difference as proportional as possible with respect to the desired electrochemical measurement variable is created across the measuring membrane. In quite general terms, a system comprising a measuring electrode and optionally an associated inner electrolyte/measuring membrane shall be referred to as measuring half-cell of an electrochemical sensor in the following, with the measuring electrode being provided in a measuring half-cell space containing also the inner electrolyte.

Due to the fact that electrical potentials always can be sensed merely as a difference from a reference potential, an electrochemical sensor always needs a measuring electrode and a further reference electrode that delivers an electrochemical reference potential as reference quantity for the measurement signal delivered from the measuring electrode. The reference electrode comprises a redox system consisting of a reference sensing electrode in contact with a reference electrolyte. The reference redox system is selected such that, upon contact of the reference sensing electrode with the reference electrolyte, a known electrochemical potential is created that is as stable as possible and permits the best possible reproduction. An arbitrary reference redox system of the type described will be referred to in quite general terms in the following as reference half-cell of an electrochemical sensor. The reference half-cell comprises a reference half-cell space containing the reference electrode and the reference electrolyte. The electrochemical potential of the reference half-cell is to be changed as little as possible by electrolytic contact of the reference electrolyte with the process medium.

Commonly used reference half-cells are based on electrodes of the second kind in which a reference sensing electrode of metal, which is coated with a not readily soluble metal salt, is in contact with a reference electrolyte containing a chemically inert salt that is readily soluble in the reference electrolyte and has the same anion as that of the not readily soluble electrolyte coating. The reference electrolyte frequently is a liquid or a rather viscous gel, in particular an aqueous saline solution or an aqueous gel of a specific salt. A redox system commonly used for reference electrodes, as it may also be provided for use with the present invention, consists, e.g., of an Ag electrode having a coating of AgCl and being immersed in a reference electrolyte of aqueous KCl. Other redox systems that are feasible for use with the present invention as well are based on iodine/iodide redox systems or calomel redox systems ($Hg/Hg_2Cl_2$), each together with suitable reference electrolytes selected on the basis of the criterion that the reference electrolyte should exhibit good electric conductivity, should be chemically neutral and the ions thereof should display as equal mobility as possible.

For determination of the respective electrochemical measurement variable, the reference half-cell has to be brought into electrolytic contact with the process medium to be investigated. It is then possible to determine a voltage difference corresponding to the difference of the electrochemical potentials between the reference half-cell and the measuring half-cell.

The respective electrochemical potential arising between measuring half-cell and process medium as well as between reference electrode and reference electrolyte is dependent on numerous factors. It is therefore necessary when putting an electrochemical sensor into operation to firstly perform a calibration with solutions or electrolytes of known ion activity (as a rule there are used standardized buffer solutions for this purpose) before the desired electrochemical measurement variable can be determined quantitatively from the voltage difference ascertained for an unknown process medium.

The electrochemical potential of the reference half-cell is sensitive with respect to environmental conditions, in particular when a reference electrode was in storage for a longer period of time. For permitting electrolytic contact of the reference electrode with the process medium, which is necessary for the measurement, the reference half-cell is in contact with its environment via an opening, a diaphragm or a similar connection. This entails the risk that the reference electrolyte either leaks or dries out in case of longer storage so that the reference electrode in part or completely is no longer in contact with reference electrolyte. This affects the equilibrium of the reference redox system so that complex measures are necessary when a sensor is put into operation before quantitative determinations are possible.

The present invention is concerned in particular with making available an improved reference electrode assembly for an electrochemical sensor of the type described. In addition thereto, an improved electrochemical sensor is to be indicated as well.

The document DE 10 2013 101 735 A1 shows a potentiometric sensor device comprising a reference electrode provided in a reference half-cell space and a measuring electrode provided in a measuring half-cell space, between which a potential difference is sensed upon electrolytic contact with a process medium. The measuring electrode comprises a measuring membrane dependent on the value of the variable to be analyzed, e.g., the pH value, of a process medium. The reference half-cell is filled with a largely dry or low-moisture substance (e.g., a dry electrolyte salt) which forms the reference electrolyte only by contact with a liquid. In this manner, at least in case of proper dry storage, there is not caused uncontrolled drying of the reference electrolyte. However, when the sensor is put into operation, the reference electrolyte has to be formed first by adding liquid, and a redox equilibrium with the reference electrode needs to be established.

In case of the potentiometric sensor shown in DE 10 2010 063 031 A1 the reference half-cell space, in the storage state, is closed off with respect to the environment by a wall and is filled with a reference electrolyte. This is to avoid that the reference electrolyte, during dry storage of the same, establishes contact with the environment and is subject to leakage, so that the reference half-cell space may possibly dry out. However, the sensor is not operable in its storage state, as the reference electrolyte cannot establish electrolytic contact with the process medium. For transferring the sensor into an operative state, there can be formed a through-opening in a wall confining the reference half-cell space, through which reference electrolyte can flow out from the reference half-cell space and thus establish electrolytic contact between the reference electrolyte and a process medium surrounding the reference half-cell space. As a means for providing the through-opening, there is provided a mechanical tool for penetrating the wall or for removing a plug or closure in the wall. The thus created through-opening as a rule can be controlled with difficulty only. Above all it is problematic that a very large opening is created in many cases through which the reference electrolyte is discharged from the reference half-cell space relatively rapidly and in uncontrolled manner. The period of operation of the sensor then may be very short and hard to predict. These problems arise in particular when liquid reference electrolytes, such as KCl, are used.

BRIEF SUMMARY

Provided herein is an improved reference electrode assembly for an electrochemical sensor, in particular a potentiometric sensor, which ensures a period of operation of enhanced definition.

In particular, there is suggested a reference electrode assembly, in particular for use with an electrochemical sensor, in particular a potentiometric sensor, of the type described hereinbefore, which is characterized by the following features: the reference electrode assembly comprises a reference half-cell space having a reference electrode provided therein. The reference half-cell space comprises a storage space in which a reference electrolyte is provided at least in a storage state of the reference electrode assembly. The reference half-cell space comprises furthermore a lock space that is permeable at least with respect to the passage of reference electrolyte into an environment of the reference half-cell space. In the storage state of the reference electrode assembly, the storage space is separated from the lock space with respect to the passage of reference electrolyte. The reference electrolyte assembly is designed such that a connection between storage space and lock space can be created that is permeable for the passage of reference electrolyte from the storage space to the lock space, in order to transfer the reference electrode assembly from the storage state to an operative state.

The reference electrode assembly constitutes in particular a reference half-cell of an electrochemical sensor. The reference half-cell space may be formed, e.g., by a casing of the reference electrode assembly. The reference electrolyte may be liquid or gel-like, in particular the reference electrolyte may be present in the form of an aqueous solution, e.g., in the form of a KCl solution as it is usually employed with Ag/AgCl electrodes (very often a 3.0 molar KCl solution is used, e.g., for pH sensors). In the storage state of the reference electrode assembly, the reference electrolyte is located in the storage space. In the storage state, the lock space need not yet be filled with reference electrolyte and preferably does not yet contain reference electrolyte or at the most will contain reference electrolyte in a largely dry form, e.g., in the form of a dry electrolyte salt. It is thus ensured that the surface of the indicating or sensing electrode of the reference electrode at all times is in electrolytic contact with the reference electrolyte so that the state of equilibrium of the redox system electrode or electrode coating to reference electrolyte remains stable also in case of long storage of the sensor. In addition thereto, it is ensured that this equilibrium is not affected by external factors during storage as the storage space is closed off with respect to the environment. A significant loss of reference electrolyte from the storage space is not to be expected also in case of long storage periods.

In the operative state of the sensor the environment of the reference electrode assembly needs to establish an electrolyte connection to a process medium to be analyzed, i.e., the reference electrolyte has to be in electrolytic contact with the process medium to be analyzed. This is necessary in order to create a closed electric circuit between measuring electrode and reference electrode in which the potential difference between measuring electrode and reference electrode results in an electric current. This circuit has an outer part in which current flows between the respective sensing electrodes of the measuring electrode and the reference electrode and through electric components for determining the electric voltage between measuring electrode and reference electrode. The circuit also has an inner part in which current flows through the reference electrolyte, the process medium and possibly an inner electrolyte of the measuring electrode. Space charges and diffusion potentials which may easily occur in particular at the connection between reference electrolyte and process medium in the inner circuit and which distort the measurement should be suppressed as far as possible. However, it should be avoided at the same time that process medium contaminates the reference electrolyte surrounding the reference electrode or that the reference electrolyte mixes with the process medium beyond a specific extent. For this reason, it is advantageous to take care by means of a suitably dimensioned throttle means that there is always present a slight outflow of reference electrolyte from the reference half-cell space into the process medium, but that this flow is just a small flow, remains stable in terms of time and above all it does not reverse during the operative period of the sensor. In case of the reference electrode assembly according to the invention, this can be effected by a suitable electrolytic connection between the lock space and the environment of the reference electrode assembly. For example, a wall surrounding the lock space may have a suitable opening and/or a suitable diaphragm, e.g., of a porous material such as ceramics, glass, platinum, or a fiber-like material, such as plastics fibers, platinum wires, metal wires, which if desired may be provided in the form of textile sheet-like structures or in the form of a ground-joint diaphragm. Such diaphragms are utilized in conventional reference half-cells for connecting the reference half-cell space to the environment and are described, for example, in Helmuth Galster, "pH-Messung" (=pH measurement), Wiley-VCH, 1990, ISBN 23527278362.

When the reference electrode assembly is immersed in the process medium to be analyzed, reference electrolyte from the lock space may then enter the process medium; in this regard, it is very well possible to define or determine the flow of the reference electrolyte discharged from the lock space and concomitantly therewith the operative period of the sensor with a nevertheless constant and sufficiently large flow of the reference electrolyte flowing from the lock space into the process medium.

For causing the reference electrolyte to enter the lock space, it is provided that a connection between storage space and lock space can be created for starting operation, with said connection being permeable for the passage of reference electrolyte from the storage space to the lock space. The thus provided splitting of the reference half-cell space into a storage space and a lock space offers the advantage that the electrolyte or fluid connection between storage space and lock space to be created upon starting operation hardly takes any longer influence on the operating properties of the sensor once this connection has been established. In particular this connection has no influence on the electrolytic contact between reference electrolyte and process medium created in operation. Rather, the flow of the reference electrolyte discharged from the lock space is determined only by the electrolyte connection provided between lock space and environment, which is, e.g., a diaphragm of the type indicated hereinbefore.

The reference electrode assembly, in the storage state, is capable of surviving a virtually unlimited period of time without damage as the reference electrolyte is stored in the storage space in a closed-off manner and constantly remains in contact with the reference electrode. Only when the storage space establishes electrolytic contact or fluid connection with the lock space does also the lock space fill with reference electrolyte so that reference electrolyte from the lock space can reach the environment of the reference electrode assembly. The flow of the reference electrolyte leaving the lock space can be adjusted quite accurately via a pre-formed opening or by providing the lock space with a diaphragm already during manufacture. It is thus possible to reliably observe a desired operative period starting from the transfer of the reference electrode assembly to the operative state. Contamination problems can be efficiently avoided by making use of a diaphragm between lock space and environment of the reference electrode assembly establishing contact with the process medium.

In terms of construction the reference electrode assembly may comprise a wall which separates the storage space from the lock space with respect to the passage of reference electrolyte and in which an opening can be formed for bringing the reference electrode assembly from the storage state to the operative state. The wall can be made of the same material as a casing constituting the storage space and the lock space. In particular, the wall can be formed integrally with this casing, e.g., of a suitable plastics material. For establishing a fluid connection between storage space and lock space, there may be provided furthermore a tool for forming an opening in the wall, in particular for piercing the wall or for removing a predetermined closure means in the wall. This tool may be associated directly with the reference half-cell assembly, e.g., in the form of a disposable tool that is releasably attached to the reference half-cell assembly and can be removed from its storage state when the reference electrode assembly is put into operation. The tool may be molded or attached, e.g., to the casing of the reference electrode assembly in such a manner that it has predetermined breaking points permitting subsequent removal of the same for putting the reference electrode assembly into operation.

The tool may comprise, e.g., at least one mandrel for piercing or penetrating the wall. As an alternative, the tool may comprise an operating member for removing a closure plug, annular gap or the like, provided in the wall.

The tool may be fixedly connected to a casing surrounding the storage space and/or the lock space, e.g., such that a tool of the type mentioned, which is provided at the tip of an operating rod, can be released from a rest position for starting operation and can then be used for piercing, penetrating the wall or for removing a closure member provided in the wall. In some embodiments the tool even can be formed as part of the reference electrode assembly, if desired even integrally with a component part of the reference electrode assembly, such as the casing of the same.

It is particularly expedient when the tool can also be operated when the reference electrode assembly is installed in an electrochemical sensor. The sensor then may remain completely assembled as long as the reference electrode assembly is in its storage state, and need not be partly disassembled again for starting operation. It is even possible to insert the sensor in a process environment already before starting operation of the same, e.g., in a process container in which a specific process is to take place. This is particularly expedient as the electrochemical sensor along with the process container can then be assembled completely long before the intended use of the same and, if desired, may also be subject to corresponding measures for cleaning, sterilization or the like. Such requirements are often present in the field of biologic, biotechnological or pharmaceutical processes in which high purity of the process environment is important.

For establishing the electrolytic contact of the reference electrolyte with the process medium to be investigated, which is necessary in operation, the lock space may have an opening that is permeable for the passage of reference electrolyte from the lock space into an environment of the reference electrode assembly. In particular, the lock space can be equipped with a diaphragm that is permeable for the passage of reference electrolyte from the lock space into an environment of the reference electrode assembly. The diaphragm establishes the electrical contact with the process medium and is designed such that only a slight, but nevertheless stable flow of reference electrolyte is discharged from the lock space. By means of suitable diaphragms it is possible to adjust a quite exactly defined flow of reference electrolyte discharged from the lock space. Moreover, a diaphragm suppresses the backflow of process medium into the lock space and possibly concomitant contamination problems.

As a rule, the diaphragm has a plurality of narrow capillaries. As soon as the lock space fills with reference electrolyte, reference electrolyte establishes contact with the diaphragm from the inside of the reference half-cell space. By way of the capillary forces acting in the diaphragm the diaphragm is filled with reference electrolyte and electrolytic contact with the process medium to be analyzed is established as soon as the diaphragm establishes contact with the process medium from outside. The permeability of the diaphragm then defines, for the reference electrode utilized, the operative period of the reference electrode assembly upon filling of the lock space with reference electrolyte. In case of the reference electrode assembly according to the invention, the lock space basically can be provided with any kind of diaphragm as used for conventional potentiometric sensors, e.g., with a diaphragm of porous materials such as ceramics, glass, sinter metal (e.g., platinum foams and the like), or plastics fibers, platinum wires, metal wires. Diaphragms having a narrow gap formed by means of glass grinding are feasible as well. As regards examples of usable diaphragms, reference is made to Helmuth Galster, "pH-Messung", Wiley-VCH, 1990, ISBN 23527278362. A diaphragm of the type mentioned can be inserted, for example, in the opening formed in the lock space.

The reference half-cell space can be made of all common materials as they are used for conventional electrochemical sensors, e.g., glass. It may be particularly advantageous when the reference half-cell space is made of plastics material. Especially for applications with particularly high purity requirements or in case of process media involving a high risk of pollution or contamination, it is desirable to use a sensor only once and to discard the same after use as contamination problems can be suppressed most safely in this manner. To make sure that the sensor is not used several times, there are frequently taken measures as far as designing the sensor as disposable component, i.e., as a component which, after one-time operation of the same, cannot be restored to the storage state and then be put into operation again. Anyway, such repeated use is to be aggravated in terms of construction such that—if at all—it is to be possible at the most at the expense of restrictions in performance.

To make sure that the redox system of reference electrode or a possibly provided coating of the reference electrode and reference electrolyte at all times remains in its state of equilibrium also in case of longer storage, it is expedient when the reference electrode extends as far as into the storage space so that the reference electrode always is wetted by the reference electrolyte. It is not necessary in this regard, and as a rule not favorable either, that the reference electrode extends as far as into the lock space since the part of the reference electrode extending as far as into the lock space, in case of dry storage, in general would not be in contact with the reference electrolyte in the storage state.

The reference electrolyte assembly in particular may be designed such that it can be sterilized by radiation, in particular in the presence of the reference electrolyte and/or in case of an electrochemical sensor inserted in a process container intended for one-time use. In the fields of biology, biotechnology or pharmacy, components and containers requiring particular sterility are often subject to radiation treatment, in particular with UV radiation in order to kill possibly present bacteria, germs or the like. It is particularly advantageous in this regard when such a sterilizing treatment takes place immediately before use of the sensor or process container for determining an electrochemical measurement variable in order to prevent that germs are introduced anew after sterilization having been effected.

As already mentioned, the present invention also relates to an electrochemical sensor, in particular a potentiometric sensor, comprising at least one measuring electrode assembly including a measuring electrode, a reference electrode assembly including a reference electrode, as well as an arrangement for sensing a potential difference between the measuring electrode and the reference electrode, with the reference electrode assembly being designed as suggested herein.

Such a sensor may be designed as double measuring cell with reference electrode assembly or reference half-cell and separate measuring electrode assembly or measuring half-cell. The reference electrode assembly, in the storage state of the sensor, then is either not electrically connected at all to the measuring electrode assembly or at the most via the external electric circuit. An inner circuit between reference electrode and measuring electrode is closed only when both the measuring electrode and the reference electrode are immersed in the process medium to be investigated, with the consequence that both the reference electrolyte establishes electrical contact with the process medium and an electrical connection is created between the process medium and an inner electrolyte of the measuring electrode or the measuring electrode itself.

In many cases, in particular also with sensors intended for one-time use only, it will be expedient to design the sensor as a single-rod measuring cell comprising a reference electrode assembly or reference half-cell and a measuring electrode assembly or measuring half-cell that are integrated in a common casing.

The reference electrode assembly, as described hereinbefore, is suitable in particular for electrochemical sensors for sensing the pH value and/or the redox potential and/or the concentrations of an ion species in an in particular liquid or gel-like process medium. Sensors of this kind are known, for example in the form of glass membrane sensors for determining the pH value of liquid or gel-like process media.

The electrochemical sensor can be designed in particular as disposable measuring cell for one-time use for measuring the pH value, redox potential and/or other measurement variables in a liquid or gel-like process medium. In that event, it is particularly advantageous when the reference electrode assembly, in a state installed in a disposable container (e.g., a disposable fermenter) of the electrochemical sensor intended for one-time use, can be sterilized by radiation.

BRIEF DESCRIPTION OF THE SEVERAL VIEWS OF THE DRAWINGS

The invention will be explained in more detail in the following by way of embodiments described with reference to the accompanying drawings. In the drawings.

DETAILED DESCRIPTION

Figure 1A:
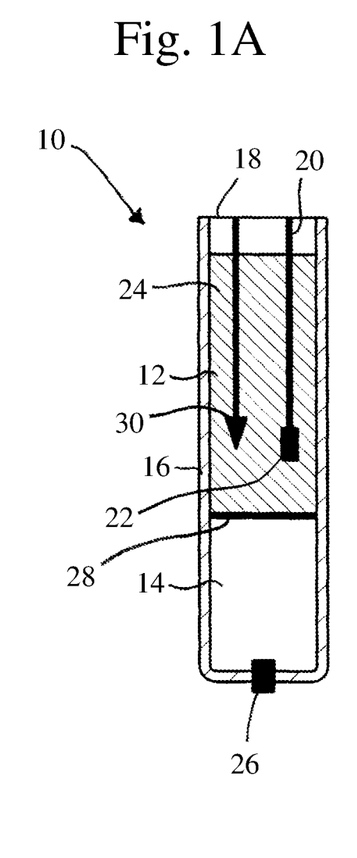
FIG. 1A shows a schematic and highly simplified representation of a reference electrode assembly according to an embodiment of the present invention in the storage state.
Figure 1B:
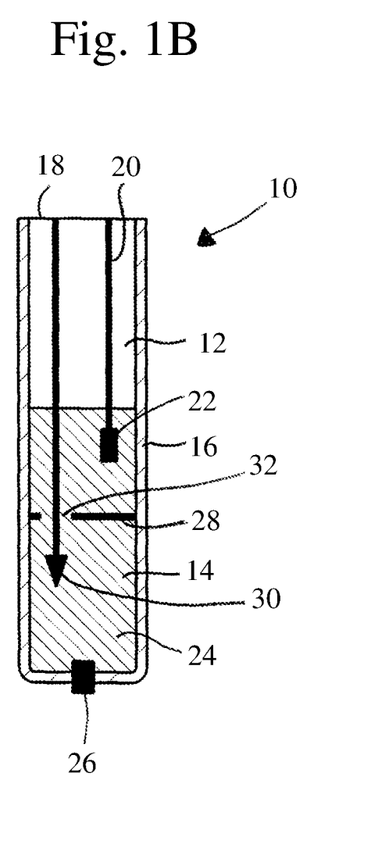
FIG. 1B shows a schematic and highly simplified representation of the reference electrode assembly of FIG. 1A in the operative state.

FIGS. 1A and 1B illustrate in schematic and highly simplified manner a reference electrode assembly 10 according to an embodiment of the present invention. FIG. 1A shows the reference electrode assembly 10 in the storage state. FIG. 1B shows the reference electrode assembly 10 in the operative state. The reference electrode assembly 10 includes a reference half-cell space comprising a storage space 12 and a lock space 14. The reference half-cell space is enclosed by a casing 16 which in the present embodiment is made of plastics material, e.g., in the form of an injection-molded part. The casing 16, on one of its narrow sides (in FIGS. 1A and 1B the top side) is closed by a lid 18 which is made of plastics material as well, in particular of the same plastics material as the casing 16. The lid 18 is penetrated by an electric lead-through 20 having an electrically conductive reference sensing electrode 22 arranged at its end extending into the interior of the casing 16. The reference sensing electrode 22 is located completely in the storage space 16 which, in the storage state illustrated in FIG. 1A, is nearly completely filled with a reference electrolyte 24, namely to such an extent that at least in the operative orientation illustrated in FIG. 1A, with the lid 18 directed upwards, the reference sensing electrode 22 is immersed completely in the reference electrolyte 24. Advantageously, the storage space 16 in the storage position according to FIG. 1A is filled with reference electrolyte to such an extent that the reference sensing electrode 22 is completely wetted with reference electrolyte 24 in any orientation of the reference sensing electrode assembly 10. The other end of the lead-through 20 penetrates the lid 18 and is electrically connected to an outer electric circuit, not shown, for determining an electrical voltage of the lead-through 20 in relation to a measuring electrode not shown in more detail. The reference sensing electrode 22 is designed as an electrode of the second kind, for example in the configuration of a metal electrode (e.g., of Ag) that is coated with AgCl and immersed in an aqueous KCl solution (e.g., a 3 molar KCl solution) as reference electrolyte 24. Alternative redox systems for the combination of reference sensing electrode 22 and reference electrolyte 24 are iodine/iodide or calomel ($Hg_2/Hg_2Cl_2$).

The lock space 14 is in fluid communication with an environment of the reference electrode assembly 10 with respect to the reference electrolyte 24 via a diaphragm 26 inserted in the casing 16. The diaphragm 24 is permeable for the reference electrolyte 24 at least in the direction outwardly from the lock space 14 into the environment of the reference electrode assembly 10, with the flow rate being adjustable substantially independently of the amount of reference electrolyte 24 in the lock space. Common diaphragms for pH sensors are described, for example, in Helmuth Galster, "pH-Messung", Wiley-VCH, 1990, ISBN 23527278362.

In the storage state illustrated in FIG. 1A, the storage space 12 is separated from the lock space 14 in fluid-tight manner as regards the reference electrolyte 24, by a partition 28. Because of the partition 28, the reference electrolyte 24 in the storage state of the reference electrode assembly 10 is present exclusively in the storage space 12, but not in the lock space 14.

Reference numeral 30 in FIGS. 1A and 1B designates a tool illustrated schematically by an arrow. Tool 30 comprises a shaft and a penetration tool arranged at the tip of the shaft, which is shown only schematically in the figures by an arrow. The penetration tool may be, for example, a mandrel that can be caused to penetrate the partition 28 by exertion of force onto the shaft, such that an opening 32 (cf. FIG. 1B) is formed in the partition through which the reference electrolyte 24 can flow from the storage space 12 into the lock space 14. The tool can also be provided in the form of a cutting tool that is adapted to cut an opening or hole of a specific size and geometry into the partition 28. Optionally, the partition 28 may be pre-designed in suitable manner to this end, for example by provision of predetermined breaking points at which the partition 28 preferably breaks when subjected to pressure. It is also conceivable that the partition 28 is provided with a closure member already in the storage state (e.g., a closure plug) which by operation of the tool 30 (with the exertion of pressure or tensile forces, if desired in combination with rotation of the tool 30 about the longitudinal axis thereof), may be pulled out or pushed out of its seat in order to thereby release an opening between storage space 12 and lock space 14. FIG. 1A indicates that the tip of the tool 30, in the storage state, is arranged in spaced apart manner from the partition 28. It would also be conceivable that the tool tip, already in the storage state according to FIG. 1A, abuts the partition 28 or is even connected to the same, at the location where the breakthrough or the opening is to be created. This considerably facilitates handling for starting operation.

As can be seen from the comparison of FIGS. 1A and 1B, the shaft of the tool 30 is fixed to the lid 18 of the reference half-cell space, in such a manner that the shaft can be urged into the interior of the reference half-cell space so as to pierce the partition 28 with the tool tip. The tool can also be made of plastics material, largely even of the same plastics material as the casing 16. In so far as the partition 30 has certain predetermined breaking points or a closure member provided therein, the tool tip may also be made of this plastics material. Otherwise it is recommendable to manufacture at least the tool tip of a somewhat harder material than the partition 28.

The comparison of FIG. 1A and FIG. 1B reveals furthermore that, after the reference electrode assembly 10 has been transferred to the operative state, the reference electrolyte 24 passes from the storage space 12 through the newly created opening 32 into lock space 14 and fills the same in the operative orientation illustrated in FIG. 1B. To this end, it is advantageous when the lock space 14, in the operative orientation, is arranged vertically below the storage space 12 as the lock space 14 then fills completely with reference electrolyte 24 by gravity. Advantageously there should be as much reference electrolyte 24 present in the storage space 12 that, also with completely filled lock space 14, the level of the reference electrolyte 24 in the storage space 12 still is so high that, in the operative orientation, the reference sensing electrode 22 remains wetted by the reference electrolyte 24 as completely as possible. The arrangement of storage space 12 and lock space 14 vertically on top of each other, with a substantially horizontal partition 30, as illustrated in FIGS. 1A and 1B is not absolutely necessary. It is also conceivable to arrange both spaces substantially vertically beside each other so that the partition 30 extends substantially vertically, or even to arrange the storage space 12 slightly below the lock space 14 (with the partition 30 then being again substantially horizontal). What is important in this regard is merely that, after formation of the breakthrough or opening 32 in the partition 30, there enters so much reference electrolyte into the lock space 14 that the diaphragm 26 provided there, which establishes a connection to the environment of the reference electrode assembly 10 that is permeable to reference electrolyte 24, is wetted with reference electrolyte 24 from the inside. Furthermore, it should be ensured that, when the lock space 14 is filled completely with reference electrolyte 24 or when the levels of reference electrolyte 24 in the lock space 14 and in the storage space 12 are equal, the reference sensing electrode 22 largely remains wetted by reference electrolyte 24.

As soon as the reference electrolyte 24 completely fills the lock space 14 or as soon as the diaphragm 26 is wetted with reference electrolyte 24 from the inside, the reference electrode assembly 10 is in the operative state.

Figure 2A:
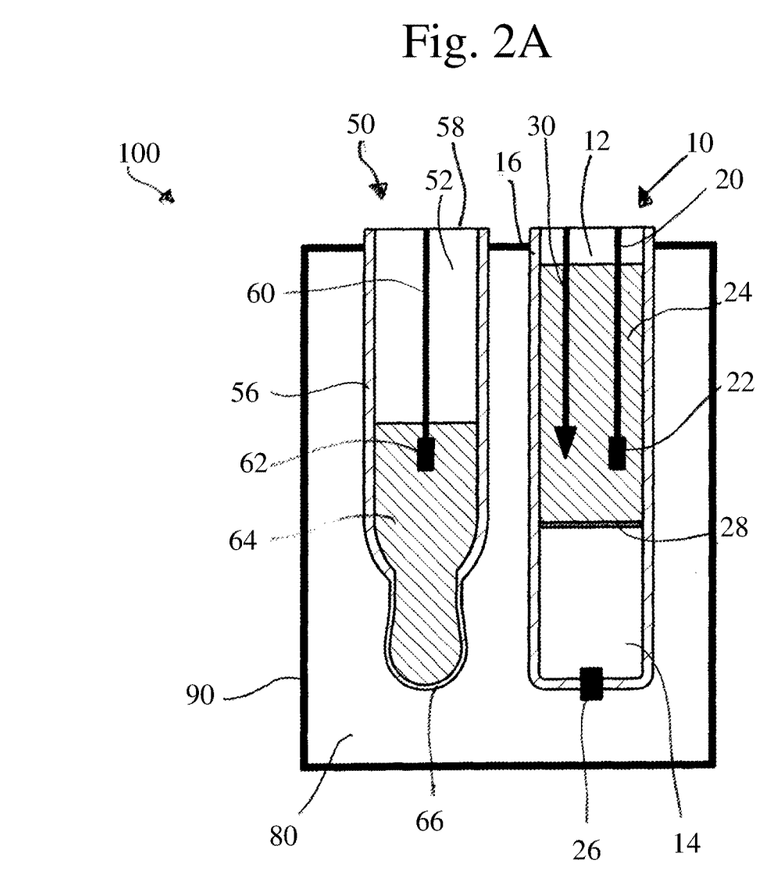
FIG. 2A shows a schematic and highly simplified representation of an electrochemical sensor designed as double cell and comprising a reference electrode assembly according to an embodiment of the present invention in the storage state.
Figure 2B:
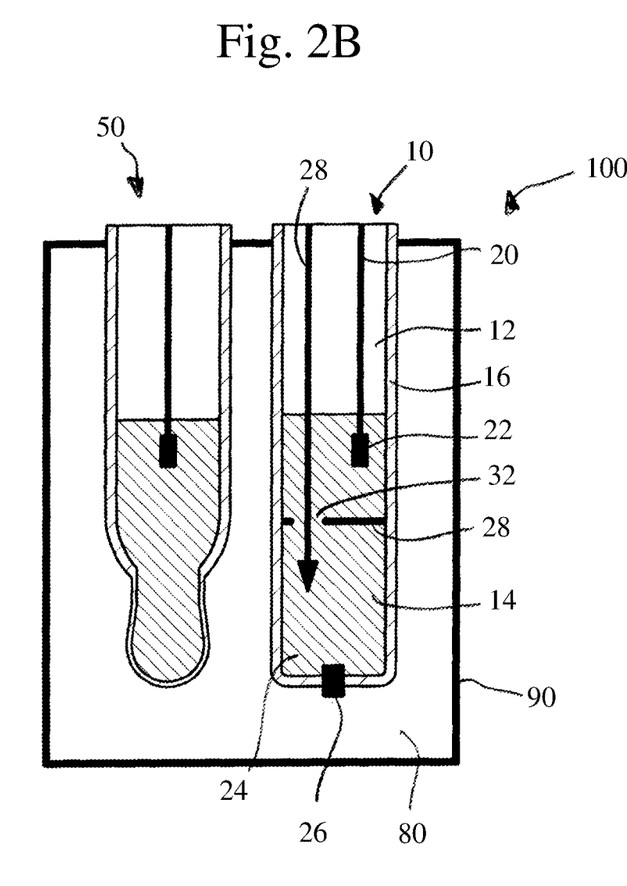
FIG. 2B shows a schematic and highly simplified representation of the electrochemical sensor of FIG. 2A in the operative state.

FIGS. 2A and 2B illustrate in schematic and highly simplified manner an electrochemical sensor 100 designed as a double-cell and comprising a reference electrode assembly 10 according to FIGS. 1A and 1B. The sensor 10 has the configuration of a double-cell, with the reference electrode assembly 10 constituting a reference half-cell, and with an additional measuring electrode assembly 50 being provided that constitutes a measuring half-cell. The measuring half-cell 50 in the measurement double-cell configuration according to FIGS. 2A/2B is formed largely independently of the reference half-cell 10. In particular, the measuring half-cell 50 is accommodated in a casing 56 of its own that is independent of the casing 16 of the reference half-cell 10. The measuring half-cell 50 and the reference half-cell 10 are coupled to each other only in so far as both thereof are accommodated in a common process container 90 containing a process medium 80 to be investigated. The casing 16 with the reference half-cell 10 just as the casing 56 with the measuring half-cell 50 may each be fixedly attached to the process container 90 and may also be stored and sterilized together with the same, e.g., by radiation with UV radiation, if desired. The transfer of the reference half-cell 10 from the storage state according to FIG. 2A into the operative state according to FIG. 2B can be effected in the installed state of the reference half-cell 10, so that there are no modifications necessary on the electrochemical sensor 100 inclusive of the process container 90.

The measuring half-cell 50 according to FIGS. 2A/2B comprises a measuring half-cell space 52 containing a measurement sensing electrode 62 and an inner electrolyte 64 therein. The measurement sensing electrode 62 is provided at the tip of a measurement lead-through 60 which projects into the interior of the measuring half-cell space 52 and is attached to a lid 58 and penetrates the same. The lid 58 and the casing 56 enclose the measuring half-cell space 52. The measurement sensing electrode 62, in the operative orientation illustrated in FIGS. 2A/2B, is immersed in the inner electrolyte 64. In the operative orientation of the measuring half-cell 50 illustrated in FIGS. 2A/2B, not only the measurement sensing electrode 62 but also an end of the measuring half-cell space 52 that is located opposite the lid 58 and in which the casing 56 forms a measuring membrane 66, is wetted with the inner electrolyte 64 from the inside. The measuring membrane 66 is immersed in the process medium 80, so that the outside of the measuring membrane 66 is wetted by the process medium 80.

In the embodiment of a pH sensor illustrated in FIGS. 2A/2B, the measuring membrane 66 may be an arbitrary membrane which, upon contact with a process medium 80 from the outside of the membrane 66, shows an electrochemical potential difference between the electrochemical potential on the inside of the membrane 66, i.e., between membrane 66 and inner electrolyte 64, and the electrochemical potential on the outside of the membrane 66, i.e., between the membrane 66 and the process medium 80. For pH sensors, there is a number of different glass membranes known fulfilling this property for different pH regions. In this context, reference is made once more to the aforementioned instructional book by Helmuth Galster, "pH-Messung", Wiley-VCH, 1990, ISBN 23527278362.

The configuration of the measuring half-cell 50 is identical for the sensor 100 in the storage state shown in FIG. 2A and the sensor 100 in the operative state shown in FIG. 2B. For the sake of clarity, reference numerals are shown only for the configuration in the storage state in FIGS. 2A and 2B; it is to be understood that the same reference numerals are also applicable for the configuration in the operative state according to FIG. 2B.

With respect to the configuration of the reference half-cell 10 in the storage state (FIG. 2A) and, respectively, upon transition to the operative state (FIG. 2B), the statements made with respect to FIGS. 1A and 1B, respectively, apply analogously so that reference is made to the description concerning these figures and being applicable to FIGS. 2A and 2B as well. It is to be noted that in FIGS. 2A and 2B just as in FIG. 3 the same reference numerals have been used for the reference half-cell 10 as in FIG. 1A/FIG. 1B.

Figure 3:
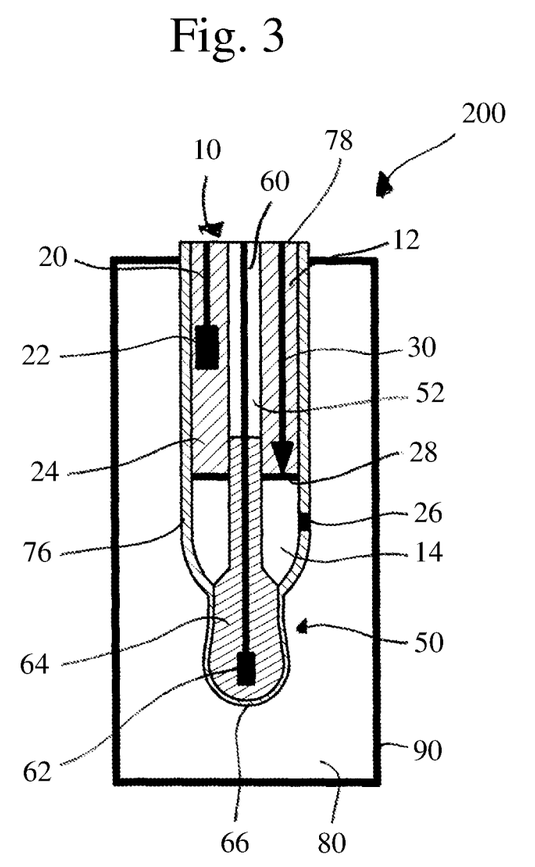
FIG. 3 shows a schematic and highly simplified representation of an electrochemical sensor designed as single-rod measuring chain and comprising a reference electrode assembly according to an embodiment of the present invention in the storage state.

FIG. 3 also shows a schematic and highly simplified representation of a further embodiment of an electrochemical sensor in the configuration of a single-rod measuring chain 200. In this sensor 200, a reference electrode assembly 10 as described before with reference to FIGS. 1A/1B, 2A/2B as well as a measuring electrode assembly 50 according to FIGS. 2A/2B are provided in a common casing 76 having a common lid 78, with the measuring electrode assembly 50, which constitutes a measuring half-cell, being arranged in an inner portion around a longitudinal axis and being surrounded in annular manner by the reference electrode assembly 10, which constitutes a reference half-cell. Reference is made once more to the description of FIGS. 1A/1B, 2A/2B, and it is to be noted that in FIG. 3 the same reference numerals have been used as in FIGS. 1A/1B, 2A/2B in so far as the same or similar components are concerned.

FIG. 3 illustrates the single-rod measuring chain 200 in a storage state according to FIGS. 1A and 2A, in which only the storage space 12 of the reference electrode assembly 10 is filled with reference electrolyte 24. Upon transfer to the operative state, the reference electrode assembly 10 according to FIG. 3 has the same configuration with the opening 32 formed in the partition 28, through which the reference electrolyte 24 enters the lock space 14, as shown in FIGS. 1B and 2B, so that reference may be made to these figures and the related description for avoiding repetitions.

It can be seen from FIG. 3 that the measuring half-cell space 52 now is surrounded in its upper part by the reference half-cell space including the storage space 12 and the lock space 14 located therebelow, and in its lower part is confined by a lower part of the common casing 76 which now constitutes the measuring membrane 66. The reference half-cell space is confined on its outside by the upper part of the casing 76 and terminates vertically above the part of the casing in which the measuring membrane 66 is formed. In this region there is also provided the diaphragm 26 at the level of the lock space 14 located below the storage space 12, via which the lock space 14 establishes electrolytic contact with a sensor environment immersed in the process medium 80.

In this manner, there is realized a sensor 200 of particularly compact construction, in which a potential difference between the measuring electrode 62 and the reference electrode 22 corresponding to the pH value in the process medium 80 can be measured in the external electric circuit.

The invention claimed is:

1. A reference electrode assembly for an electrochemical sensor, the reference electrode assembly comprising:
   a reference half-cell space having a reference electrode provided therein,
   the reference half-cell space comprising a storage space in which a reference electrolyte is provided in a storage state of the reference electrode assembly, wherein the reference electrode extends into the storage space,
   the reference half-cell space further comprising a lock space that is permeable with respect to the passage of reference electrolyte into an environment of the reference half-cell space,
   the storage space, in the storage state of the reference electrode assembly, being separated from the lock space with respect to the passage of reference electrolyte, and
   the reference electrode assembly being designed such that a connection permeable for the passage of reference electrolyte from the storage space to the lock space can be created between the storage space and the lock space in order to transfer the reference electrode assembly from the storage state to an operative state.

2. The reference electrode assembly of claim 1, further comprising at least one wall separating the storage space from the lock space with respect to the passage of reference electrolyte, said wall being adapted to have an opening formed therein to bring the reference electrode assembly from the storage state to the operative state.

3. The reference electrode assembly of claim 2, further comprising a tool for forming said opening in the wall.

4. The reference electrode assembly of claim 3, wherein when the reference electrode assembly is installed in an electrochemical sensor, the tool is adapted to be operated.

5. The reference electrode assembly of claim 3, wherein said tool is designed as part of the reference electrode assembly.

6. The reference electrode assembly of claim 3, wherein the tool is configured to pierce the wall or to remove a predetermined closure member in the wall.

7. The reference electrode assembly of claim 1, wherein the lock space comprises an opening that is permeable for the passage of reference electrolyte from the lock space into an environment of the reference electrode assembly.

8. The reference electrode assembly of claim 1, wherein the lock space comprises a diaphragm that is permeable for the passage of reference electrolyte from the lock space into an environment of the reference electrode assembly.

9. The reference electrode assembly of claim 8, wherein the lock space comprises an opening that is permeable for the passage of reference electrolyte from the lock space into an environment of the reference electrode assembly, and wherein the diaphragm is inserted into the opening formed in the lock space.

10. The reference electrode assembly of claim 1, further comprising a plastics casing.

11. The reference electrode assembly of claim 1, wherein the reference electrode assembly is adapted to be sterilized by radiation.

12. An electrochemical sensor, comprising:
    at least one measuring electrode assembly including a measuring electrode,
    a reference electrode assembly including a reference electrode, and
    an arrangement for sensing a potential difference between the measuring electrode and the reference electrode,
    wherein the reference electrode assembly is the reference electrode assembly of claim 1.

13. The electrochemical sensor of claim 12, wherein the electrochemical sensor is designed as a double measuring cell including a reference electrode assembly and a separate measuring electrode assembly.

14. The electrochemical sensor of claim 12, wherein the sensor is designed as a single-rod measuring cell including a reference electrode assembly and a measuring electrode assembly that are integrated in a common casing.

15. The electrochemical sensor of claim 12, wherein the sensor is designed for sensing at least one of the pH value, the redox potential, and the concentrations of an ion species in a liquid process medium.

16. The electrochemical sensor of claim 12, wherein the sensor is designed as a disposable measuring cell for one-time use for measuring at least one of the pH value, redox potential, and other measurement variables in a liquid process medium.

17. The electrochemical sensor of claim 12, wherein the electrochemical sensor is a potentiometric sensor.

18. The reference electrode assembly of claim 1, wherein the reference electrode assembly is adapted to be sterilized by radiation in the presence of the reference electrolyte and/or when the reference electrode assembly is installed in a disposable container of an electrochemical sensor intended for one-time use.

* * * * *